(12) United States Patent
Zacuto et al.

(10) Patent No.: US 9,187,488 B2
(45) Date of Patent: Nov. 17, 2015

(54) PROCESS FOR PREPARING CHIRAL DIPEPTIDYL PEPTIDASE-IV INHIBITORS

(75) Inventors: Michael J. Zacuto, Jersey City, NJ (US); Robert F. Dunn, Towaco, NJ (US); Aaron J. Moment, Middletown, NJ (US); Jacob M. Janey, New York, NY (US); David Lieberman, Hoddesdon (GB); Faye Sheen, Hoddesdon (GB); Nadine Bremeyer, Hoddesdon (GB); Jeremy Scott, Hoddesdon (GB); Jeffrey T. Kuethe, Somerset, NJ (US); Lushi Tan, Edison, NJ (US); Qinghao Chen, Edison, NJ (US)

(73) Assignees: Merck Sharp & Dohme Corp, Rahway, NJ (US); Merck Sharp & Dohme Ltd., Hoddesdon (GB)

(*) Notice: Subject to any disclaimer, the term of this patent is extended or adjusted under 35 U.S.C. 154(b) by 0 days.

(21) Appl. No.: 14/119,063

(22) PCT Filed: Jun. 25, 2012

(86) PCT No.: PCT/US2012/043924
§ 371 (c)(1),
(2), (4) Date: Nov. 20, 2013

(87) PCT Pub. No.: WO2013/003250
PCT Pub. Date: Jan. 3, 2013

(65) Prior Publication Data
US 2014/0107346 A1    Apr. 17, 2014

Related U.S. Application Data

(60) Provisional application No. 61/502,497, filed on Jun. 29, 2011.

(51) Int. Cl.
| C07D 487/04 | (2006.01) |
| A61K 31/4439 | (2006.01) |
| A61K 31/4985 | (2006.01) |
| A61K 31/513 | (2006.01) |

(52) U.S. Cl.
CPC .......... *C07D 487/04* (2013.01); *A61K 31/4439* (2013.01); *A61K 31/4985* (2013.01); *A61K 31/513* (2013.01); *C07B 2200/13* (2013.01)

(58) Field of Classification Search
CPC .................................................... C07D 487/04
See application file for complete search history.

(56) References Cited

U.S. PATENT DOCUMENTS

| 5,041,442 A | 8/1991 | Romero et al. |
| 2005/0032804 A1 | 2/2005 | Cypes et al. |
| 2010/0120863 A1 | 5/2010 | Biftu et al. |
| 2010/0234607 A1 | 9/2010 | Jung et al. |

FOREIGN PATENT DOCUMENTS

| CN | 1429805 A | 7/2003 |
| CN | 1438211 A | 8/2003 |
| CN | 101031300 A | 9/2007 |
| WO | WO02076450 A1 | 10/2002 |
| WO | WO03000180 A2 | 1/2003 |
| WO | WO03000181 A2 | 1/2003 |
| WO | WO03004498 A1 | 1/2003 |
| WO | WO03082817 A2 | 10/2003 |
| WO | WO2004007468 A1 | 1/2004 |
| WO | WO2004032836 A2 | 4/2004 |
| WO | WO2004037169 A2 | 5/2004 |
| WO | WO2004043940 A1 | 5/2004 |
| WO | WO2004050022 A2 | 6/2004 |
| WO | WO2004058266 A1 | 7/2004 |
| WO | WO2004064778 A2 | 8/2004 |
| WO | WO2004069162 A2 | 8/2004 |
| WO | WO2004103276 A2 | 12/2004 |
| WO | WO2004110436 A1 | 12/2004 |
| WO | WO2004112701 A2 | 12/2004 |
| WO | WO2005011581 A2 | 2/2005 |
| WO | WO2005044195 A2 | 5/2005 |
| WO | WO2005108382 A1 | 11/2005 |
| WO | WO2005116029 A1 | 12/2005 |

(Continued)

*Primary Examiner* — Samantha Shterengarts
(74) *Attorney, Agent, or Firm* — Janet E. Fair; Anna L. Cocuzzo

(57) ABSTRACT

A process for the preparation of pyrazolopyrolidines of structural formula I: and W is or P, wherein in P is an amine protecting group. These compounds are useful in the synthesis of dipeptidyl peptidase-IV inhibitors for the treatment of Type 2 diabetes. Also provided are useful intermediates obtained from the process.

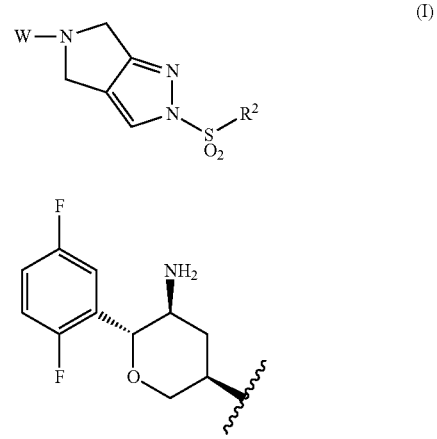

10 Claims, No Drawings

(56) References Cited

FOREIGN PATENT DOCUMENTS

| | | |
|---|---|---|
| WO | WO2006009886 A1 | 1/2006 |
| WO | WO2006023750 A2 | 3/2006 |
| WO | WO2006039325 A2 | 4/2006 |
| WO | WO2006065826 A2 | 6/2006 |
| WO | WO2006078676 A2 | 7/2006 |
| WO | WO2006104997 A2 | 10/2006 |
| WO | WO2006119260 A2 | 11/2006 |
| WO | WO2006127530 A2 | 11/2006 |
| WO | WO2007024993 A2 | 3/2007 |
| WO | WO2007035198 A2 | 3/2007 |
| WO | WO2007070434 A2 | 6/2007 |
| WO | WO2007078726 A2 | 7/2007 |
| WO | WO2007087231 A2 | 8/2007 |
| WO | WO2007097931 A2 | 8/2007 |
| WO | WO2007126745 A2 | 11/2007 |
| WO | WO2007136603 A2 | 11/2007 |
| WO | WO2008060488 A1 | 5/2008 |
| WO | WO2009025784 A1 | 2/2009 |
| WO | WO2010056708 A1 | 5/2010 |
| WO | WO2011028455 A1 | 3/2011 |
| WO | WO2011037793 A1 | 3/2011 |
| WO | WO2011146358 A1 | 11/2011 |

PROCESS FOR PREPARING CHIRAL DIPEPTIDYL PEPTIDASE-IV INHIBITORS

CROSS REFERENCE TO RELATED APPLICATIONS

This application is the National Stage of International Application No. PCT/US2012/043924, filed 26 Jun. 2012, which claims the benefit under 35 U.S.C. 119(e) of U.S. Provisional Application No. 61/502,497, filed 29 Jun. 2011.

FIELD OF THE INVENTION

The present invention is directed to a novel process for the preparation of pyrazolopyrolidines which are useful intermediates in making dipeptidyl peptidase-IV (DPP-4) inhibitors for the treatment of Type 2 diabetes.

BACKGROUND OF THE INVENTION

The present invention is directed to novel synthetic methods in the manufacture of pharmaceutically active pyrazolopyrolidines, and pyrazolopyrolidine intermediates in the manufacture of pharmaceutically active compounds. The present invention is further directed to intermediates useful in the disclosed process.

The synthesis of pyrazolopyrolidines has previously been described in PCT international patent application WO 2010/056708. The syntheses taught in Intermediate 6 of WO 2010/056708 yielded a 1:1 mixture of products of formulas Ia and Ib.

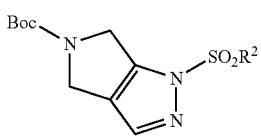

Ia

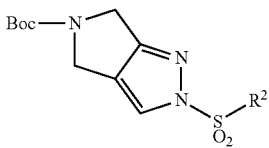

Ib

WO 2010/056708 taught an additional step of resolution of the desired product Ib by column chromatography.

The pyrazolopyrolidines of structural formula Ib described in WO 2010/056708 are used in processes to synthesize effective DPP-IV inhibitors, such as formula IIb:

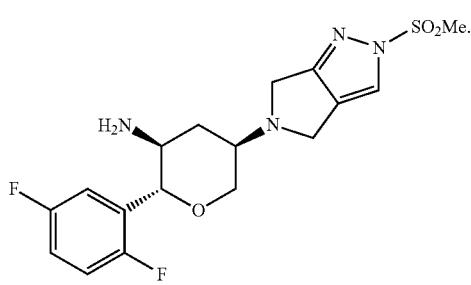

IIb

A regioisomer-selective process, yielding a greater percentage of the desired pyrazolopyrolidine regioisomer product, was desired. The inventors have now discovered efficient regioisomer-selective processes, comprising sulfonylation of the pyrazolopyrolidines and isomerization of the sulfonylated pyrazolopyrolidines.

SUMMARY OF THE INVENTION

This invention is concerned with a process for preparing regioisomer-selective pyrazolopyrolidines of structural formula I:

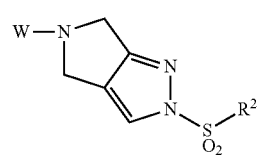

I wherein $R^2$ is selected from the group consisting of:
$C_{1-6}$ alkyl and $C_{3-6}$ cycloalkyl; and
W is selected from the group consisting of hydrogen; P, wherein in P is an amine protecting group; and

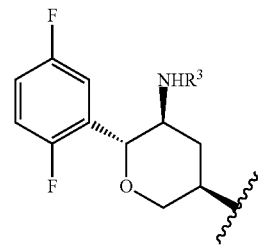

wherein $R^3$ is hydrogen or P, wherein in P is an amine protecting group;

The process comprises sulfonylation of the pyrazolopyrolidines and isomerization of the sulfonylated pyrazolopyrolidines. Depending on the reaction conditions, the process can be done as a single-step process or a two-step process.

In certain embodiments, the sulfonylation is specifically mesylation. In certain embodiments, wherein the process is a single-step i.e. "one pot" process, the process comprises mesylation of the pyrazolopyrolidines and isomerization of the mesylated pyrazolopyrolidines. In other embodiments, wherein the process is a two-step process, the first step is mesylation of the pyrazolopyrolidines and the second step is isomerization of the mesylated pyrazolopyrolidines.

Also described herein are novel salts derived from pyrazolopyrolidines of structural formula I, wherein W is H. Such salts can be used in the preparation of dipeptidyl peptidase-IV (DPP-4) inhibitors of structural formula II, as described in WO 2010/056708.

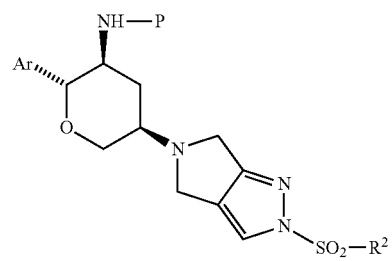

wherein Ar is phenyl optionally substituted with one to five $R^1$ substituents;
each $R^1$ is independently selected from the group consisting of:
  fluorine,
  chlorine,
  $C_{1-6}$ alkyl, optionally substituted with one to five fluorines, and
  $C_{1-6}$ alkoxy, optionally substituted with one to five fluorines.

Such DPP-IV inhibitors of formula II are useful for the treatment of Type 2 diabetes. The DPP-4 inhibitors can be synthesized by reductive amination of the tetrahydropyran-5-ones and removal of the primary amine protecting group.

DETAILED DESCRIPTION OF THE INVENTION

The process of the present invention involves the preparation of a compound of structural formula I:

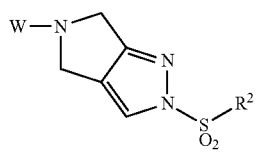

wherein $R^2$ is selected from the group consisting of:
  $C_{1-6}$ alkyl and $C_{3-6}$ cycloalkyl; and
W is selected from the group consisting of hydrogen; P, wherein in P is an amine protecting group; and

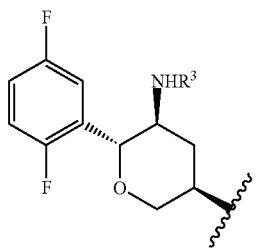

wherein $R^3$ is hydrogen or P; wherein in P is an amine protecting group;
comprising:
(a) sulfonylation of a compound of formula III:

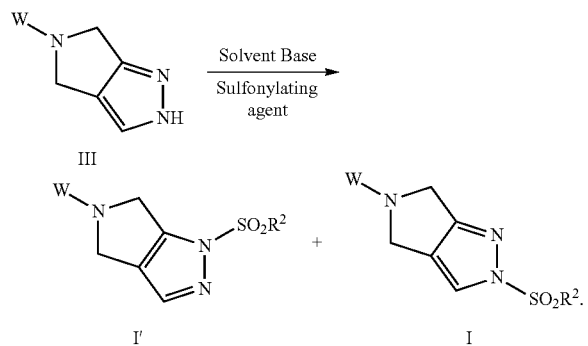

(b) isomerization of the sulfonylated formula III;

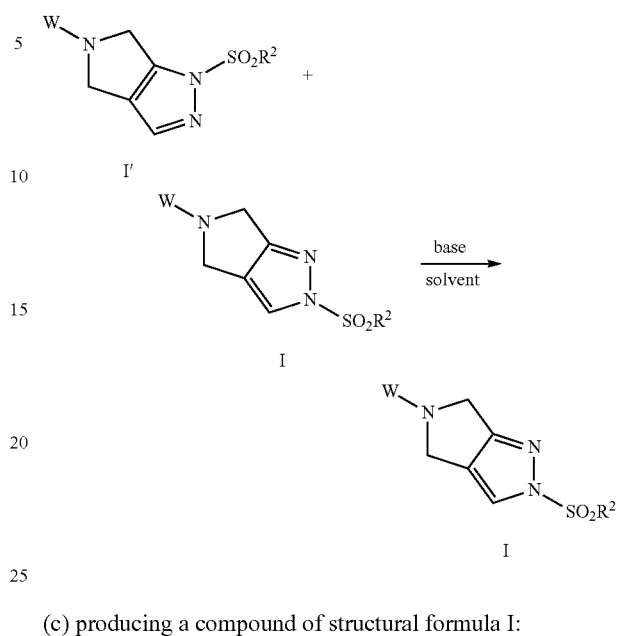

(c) producing a compound of structural formula I:

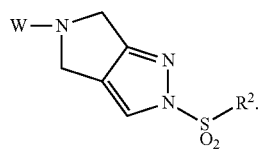

As used in the structural formulas of the compounds described herein, P is an amine protecting group. Examples of suitable primary amine protecting groups include, but are not limited to, t-butyloxycarbonyl (Boc), benzyloxycarbonyl (CBz), 9-fluorenylmethyl-oxycarbonyl (FMOC), allyloxycarbonyl (Allyloc), methoxycarbonyl, ethocycarbonyl acetyl, formyl, phthaloyl, benzoyl, phenyl, lower alkyl, such as methyl, ethyl or t-butyl and pivaloyl. One embodiment of the amine protecting group is Boc which is removable under acidic conditions, such as aqueous HCl, sulfuric acid, HBr, $HBF_4$, benzenesulfonic acid, p-toluenesulfonic acid, methanesulfonic acid, and trifluoroacetic acid in an organic solvent.

Also described herein is a process for the preparation of a compound of structural formula Ic:

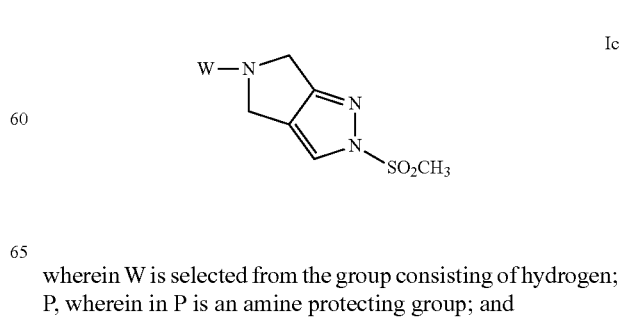

wherein W is selected from the group consisting of hydrogen; P, wherein in P is an amine protecting group; and

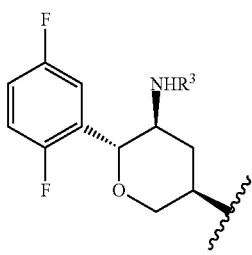

wherein $R^3$ is hydrogen or P; wherein in P is an amine protecting group;
comprising:
(a) mesylation of a compound of formula III:

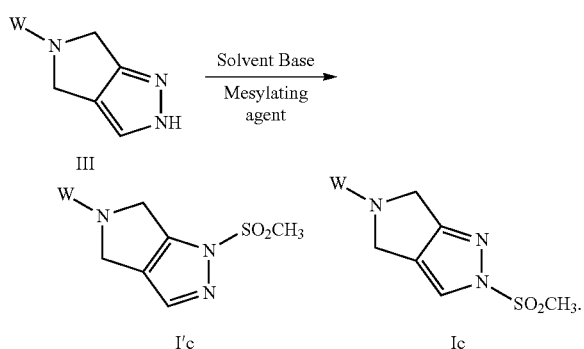

(b) isomerization of the mesylated formula III;

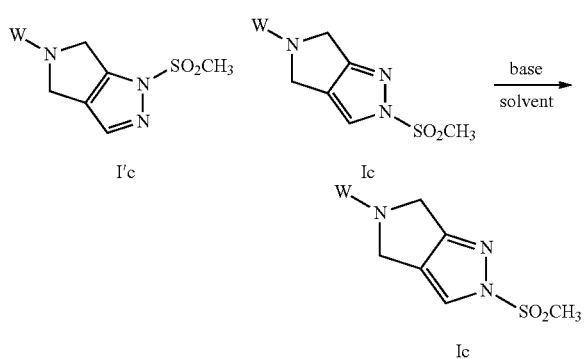

(c) producing a compound of structural formula Ic:

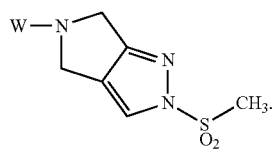

The sulfonylation or mesylation and isomerization of the sulfonylated or mesylated pyrazolopyrolidines, depending on the reaction conditions, can be done in a single-step process or a two-step process.

Single-Step Process

In certain embodiments, the process described herein is a single-step process, wherein a pyrazolopyridine, such as a compound of formula III is sulfonylated and the sulfonylated pyrazolopyridine is further isomerized in a single-step i.e. "one pot" process. The single-step comprises combining a pyrazolopyrolidone, such as a compound of formula III with a sulfonylating agent and at least one base in a suitable solvent.

In certain embodiments, the process is a single-step process, wherein a pyrazolopyridine, such as a compound of formula III is mesylated and the mesylated pyrazolopyridine is further isomerized in a single-step i.e. "one pot" process. The single-step comprises combining a pyrazolopyrolidone, such as a compound of formula III with a mesylating agent and base in a suitable solvent system.

Suitable sulfonylating agents include, but are not limited to, $R^2SO_2Cl$, $R^2SO_2Br$ and $R^2SO_2$—O—$SO_2R^2$,

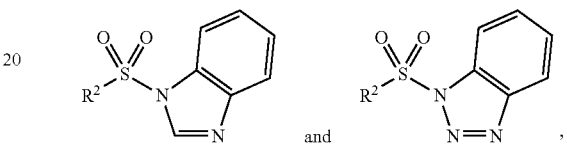

wherein $R^2$ is selected from the group consisting of $C_{1-6}$ alkyl and $C_{3-6}$ cycloalkyl. In the instance wherein $R^2$ is an alkyl, suitable alkyls include, but are not limited to, methyl, ethyl, propyl, butyl, pentyl and hexyl. In the instance wherein $R^2$ is a cycloalkyl, suitable cycloalkyls include, but are not limited to, cyclopropyl, cyclobutyl, cyclopentyl and cyclohexyl.

Suitable mesylating agents include, but are not limited to, MsCl, MsBr, Ms-O-Ms,

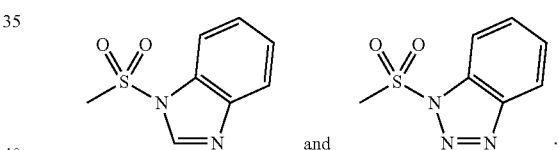

A particular suitable mesylating agent for the single-step process is MsCl.

Suitable bases include, but are not limited to, TMG, LDA, $Cs_2CO_3$, $K_3PO_4$, $Na_2CO_3$, $K_2CO_3$, iPrMgCl, TEA, DABCO, DMAP, DBU, KOtBu, Hunig's base ($iPr_2NEt$), NaHMDS, $Cs_2CO_3$. A particularly suitable base for the single-step process is TEA or NaHMDS.

Suitable solvents include, but are not limited to, EtOAc, IPAc, NMP, DMF, DMAc, IPA, MeCN, MeOH, MTBE, PhMe, THF, MeTHF and combinations thereof. Particular suitable solvents include MeTHF, THF and DMAc. Particularly suitable solvents for the single-step process are THF and DMAc or combinations thereof.

In certain embodiments, wherein the process is a single-step process comprising sulfonylation or mesylation of the pyrazolopyrolidine, such as the compound of formula III and isomerizing the sulfonylated or mesylated pyrapolopyridine, the single-step comprises combining pyrazolopyrolidine, such as the compound of formula III the with a sulfonylating or mesylating agent and a base in a suitable organic solvent such that greater than 70% of the pyrazolopyrolidine, such as the compound of formula III is converted to the desired sulfonated or mesylated isomer, such as formula I. In another embodiment, greater than 75% of the pyrazolopyrolidine, such as the compound of formula III is converted to the desired sulfonated or mesylated isomer, such as formula I. In another embodiment, greater than 80% of the pyrazolopyrolidine, such as the compound of formula III is converted to the desired sulfonated or mesylated isomer, such as formula I. In another embodiment, greater than 85% of the pyrazolopyrolidine, such as the compound of formula III is converted to the desired sulfonated or mesylated isomer, such as formula I. In another embodiment, greater than 90% of the pyrazolopyrolidine, such as the compound of formula III is converted to the desired sulfonated or mesylated isomer, such as formula I. In another embodiment, greater than 91% of the pyrazolopyrolidine, such as the compound of formula III is converted to the desired sulfonated or mesylated isomer, such as formula I. In another embodiment, greater than 92% of the pyrazolopyrolidine, such as the compound of formula III is converted to the desired sulfonated or mesylated isomer, such as formula I. In another embodiment, greater than 93% of the pyrazolopyrolidine, such as the compound of formula III is converted to the desired sulfonated or mesylated isomer, such as formula I. In another embodiment, greater than 94% of the pyrazolopyrolidine, such as the compound of formula III is converted to the desired sulfonated or mesylated isomer, such as formula I. In another embodiment, greater than 95% of the pyrazolopyrolidine, such as the compound of formula III is converted to the desired sulfonated or mesylated isomer, such as formula I.

In one embodiment the compound of formula III is combined with MsCl and NaHMDS in THF and DMAc until greater than 70% of formula III is converted to formula Ic. In one embodiment the compound of formula III is combined with MsCl and NaHMDS in THF and DMAc until greater than 75% of formula III is converted to formula Ic. In one embodiment the compound of formula III is combined with MsCl and NaHMDS in THF and DMAc until greater than 80% of formula III is converted to formula Ic. In one embodiment the compound of formula III is combined with MsCl and NaHMDS in THF and DMAc until greater than 85% of formula III is converted to formula Ic. In one embodiment the compound of formula III is combined with MsCl and NaHMDS in THF and DMAc until greater than 90% of formula III is converted to formula Ic. In one embodiment the compound of formula III is combined with MsCl and NaHMDS in THF and DMAc until greater than 91% of formula III is converted to formula Ic. In one embodiment the compound of formula III is combined with MsCl and NaHMDS in THF and DMAc until greater than 92% of formula III is converted to formula Ic. In one embodiment the compound of formula III is combined with MsCl and NaHMDS in THF and DMAc until greater than 93% of formula III is converted to formula Ic. In one embodiment the compound of formula III is combined with MsCl and NaHMDS in THF and DMAc until greater than 94% of formula III is converted to formula Ic. In one embodiment the compound of formula III is combined with MsCl and NaHMDS in THF and DMAc until greater than 95% of formula III is converted to formula Ic.

Two-Step Process

In other embodiments the process is a two-step process wherein the first step comprises sulfonylation of the pyrazolopyrolidone, such as a compound of formula III. The sulfonylation step comprises combining the pyrazolopyrolidone with a sulfonylating agent and a first base in a suitable first organic solvent. The second step is isomerization of the sulfonylated pyrazolopyrolidines comprising combining sulfonylated pyrazolopyrolidine with a second base in a suitable second organic solvent.

In other embodiments the process is a two-step process wherein the first step in the process of the present invention is mesylation of the pyrazolopyrolidine, such as the compound of formula III. In one embodiment the first step in the process of the present invention is mesylation of the pyrazolopyrolidine, such as the compound of formula III is combined with a mesylating agent and a first base in a suitable first organic solvent.

Suitable sulfonylating agents include, but are not limited to, $R^2SO_2Cl$, $R^2SO_2Br$ and $R^2SO_2Cl$—O—$R^2SO_2Cl$,

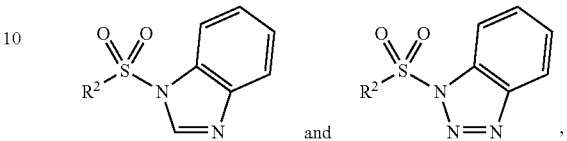

wherein $R^2$ is selected from the group consisting of $C_{1-6}$ alkyl; and $C_{3-6}$ cycloalkyl. In the instance wherein $R^2$ is an alkyl, suitable alkyls include, but are not limited to, methyl, ethyl, propyl, butyl, pentyl and hexyl. In the instance wherein $R^2$ is a cycloalkyl, suitable cycloalkyls include, but are not limited to, cyclopropyl, cyclobutyl, cyclopentyl and cyclohexyl.

Suitable mesylating agents include, but are not limited to, MsCl, MsBr, Ms-O-Ms,

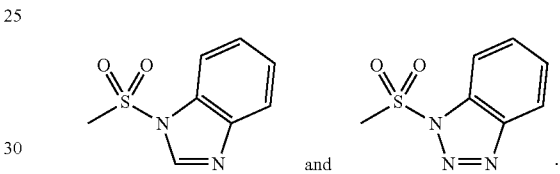

A particular suitable mesylating agent for the two-step process is MsCl.

Suitable first bases include, but are not limited to, TMG, LDA, $Cs_2CO_3$, $K_3PO_4$, $Na_2CO_3$, $K_2CO_3$, iPrMgCl, TEA, DABCO, DMAP, DBU, KOtBu, Hunig's, NaHMDS, $Cs_2CO_3$. A particularly suitable first base for the sulfonylation step is TEA, KOtBu or NaHMDS. A particularly suitable first base for the mesylation step is TEA, KOtBu or NaHMDS. A particularly suitable first base for the two-step process is KOtBu.

Suitable first solvents include, but are not limited to, EtOAc, IPAc, NMP, DMF, DMAc, IPA, MeCN, MeOH, MTBE, PhMe, THF, MeTHF and combinations thereof. Particular suitable first solvents include MeTHF, THF and DMAc. Particularly suitable first solvents for the two-step process, is MeTHF.

In the embodiments wherein the process is a two-step process, the first step in the process of the present invention is sulfonylation or mesylation of the pyrazolopyrolidine, such as the compound of formula III by combining formula III with a sulfonylating or mesylating agent and a first base in a suitable first organic solvent such that greater than 90% of the pyrazolopyrolidine, such as the compound of formula III is converted to the sulfonylated or mesylated compound, such as those of compounds I' and I or I'c and Ic. In another embodiment, greater than 91% of the pyrazolopyrolidine is converted to the sulfonylated or mesylated compound. In another embodiment, greater than 92% of the pyrazolopyrolidine is converted to the sulfonylated or mesylated compound. In another embodiment, greater than 93% of the pyrazolopyrolidine is converted to the sulfonylated or mesylated compound. In another embodiment, greater than 94% of the pyrazolopyrolidine is converted to the sulfonylated or mesylated compound. In another embodiment, greater than 95% of the pyrazolopyrolidine is converted to the sulfonylated or mesylated compound. In another embodiment, greater than 96% of the pyrazolopyrolidine is converted to the sulfonylated or mesylated compound. In another embodiment, greater than 97% of the pyrazolopyrolidine is converted to the sulfonylated or mesylated compound. In another embodiment, greater than 98% of the pyrazolopyrolidine is converted to the sulfonylated or mesylated compound. In another embodiment, greater than 99% of the pyrazolopyrolidine is converted to the sulfonylated or mesylated compound.

In one embodiment, wherein in the process is a two-step process, the first step is mesylation of formula III, by adding MsCl to a mixture of formula III and triethylamine in MeTHF until greater than 90% conversion to compounds Ic' and Ic is obtained. In another embodiment, formula III is added to a mixture of MsCl, and triethylamine in MeTHF until greater than 91% conversion to compounds Ic' and Ic is obtained. In another embodiment, formula III is added to a mixture of MsCl, and triethylamine in MeTHF until greater than 92% conversion to compounds Ic' and Ic is obtained. In another embodiment, formula III is added to a mixture of MsCl, and triethylamine in MeTHF until greater than 93% conversion to compounds Ic' and Ic is obtained. In another embodiment, formula III is added to a mixture of MsCl, and triethylamine in MeTHF until greater than 94% conversion to compounds Ic' and Ic is obtained. In another embodiment, formula III is added to a mixture of MsCl, and triethylamine in MeTHF until greater than 95% conversion to compounds Ic' and Ic is obtained.

In another embodiment, formula III is added to a mixture of MsCl, and triethylamine in MeTHF until greater than 96% conversion to compounds Ic' and Ic is obtained. In another embodiment, formula III is added to a mixture of MsCl, and triethylamine in MeTHF until greater than 97% conversion to compounds Ic' and Ic is obtained. In another embodiment, formula III is added to a mixture of MsCl, and triethylamine in MeTHF until greater than 98% conversion to compounds Ic' and Ic is obtained. In another embodiment, formula III is added to a mixture of MsCl, and triethylamine in MeTHF until greater than 99% conversion to compounds Ic' and Ic is obtained.

In one embodiment, wherein the process is a two-step process, the second step is isomerization of the sulfonylated pyrazolopyrolidines, such as the compounds of formula I' and I with a suitable second base in a suitable second organic solvent. In one embodiment the second step in the process of the present invention is isomerization of the mesylated pyrazolopyrolidine, such as the compounds of formula Ic' and Ic with a suitable second base in a suitable second organic solvent.

Suitable second bases for the isomerization steps include, but are not limited to, TMG, LDA, $Cs_2CO_3$, LDA, $K_3PO_4$, NaHMDS, $Na_2CO_3$, $K_2CO_3$, iPrMgCl, TEA, DABCO, DMAP, DBU, NaOtBu, KOtBu, $Bu_4N^+OH^-$, Hunig's, NaOH. A particularly suitable second base for the isomerization step is NaHMDS or KOtBu.

Suitable second solvents include, but are not limited to, EtOAc, IPAc, NMP, DMF, DMAc, IPA, MeCN, MeOH, MTBE, PhMe, THF, MeTHF and combinations thereof. A particular suitable second solvent is DMAc.

In one embodiment, a suitable second base is added to a mixture of I' and I and second solvent until greater than 70% conversion of I' and I to I is obtained. In one embodiment, a mixture of I' and I is added to a suitable second base and second solvent until greater than 75% conversion of I' and I to I is obtained. In one embodiment, a suitable second base is added to a mixture of I' and I and second solvent until greater than 80% conversion of I' and I to I is obtained. In one embodiment, a mixture of I' and I is added to a suitable second base and second solvent until greater than 85% conversion of I' and I to I is obtained. In one embodiment, a mixture of I' and I to I is added to a suitable second base and second solvent until greater than 90% conversion of I' and I to I is obtained. In one embodiment, a mixture of I' and I is added to a suitable second base and second solvent until greater than 95% conversion of I' and I to I is obtained. In one embodiment, a mixture of I' and I is added to a suitable second base and second solvent until greater than 96% conversion of I' and I to I is obtained. In one embodiment, a mixture of I' and I is added to a suitable second base and second solvent until greater than 96% conversion of I' and I to I is obtained. In one embodiment, a mixture of I' and I is added to a suitable second base and second solvent until greater than 97% conversion of I' and I to I is obtained. In one embodiment, a mixture of I' and I is added to a suitable second base and second solvent until greater than 98% conversion of I' and I to I is obtained. In one embodiment, a mixture of I' and I is added to a suitable second base and second solvent until greater than 99% conversion of I' and I to I is obtained.

Methods of Making DPP-IV Inhibitors

The invention is further directed to the manufacture of DPP IV inhibitors of formula IIa

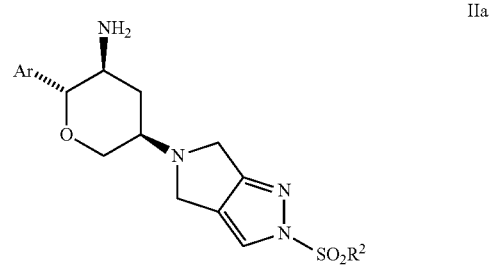

wherein Ar is phenyl optionally substituted with one to five $R^1$ substituents;

each $R^1$ is independently selected from the group consisting of:
  fluorine,
  chlorine,
  $C_{1-6}$ alkyl, optionally substituted with one to five fluorines, and
  $C_{1-6}$ alkoxy, optionally substituted with one to five fluorines;

$R^2$ is selected from the group consisting of:
  $C_{1-6}$ alkyl; and
  $C_{3-6}$ cycloalkyl, comprising the step of forming a salt of formula I, when W is H; and $R^2$ is selected from the group consisting of:
  $C_{1-6}$ alkyl and $C_{3-6}$ cycloalkyl;

forming a compound of formula II through reductive amination of formula Ih and a ketone of formula IV; and removing the protecting group of formula II to form a compound of formula IIa.

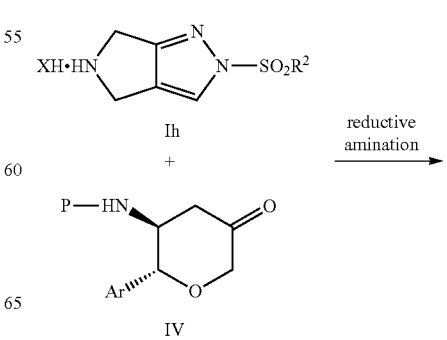

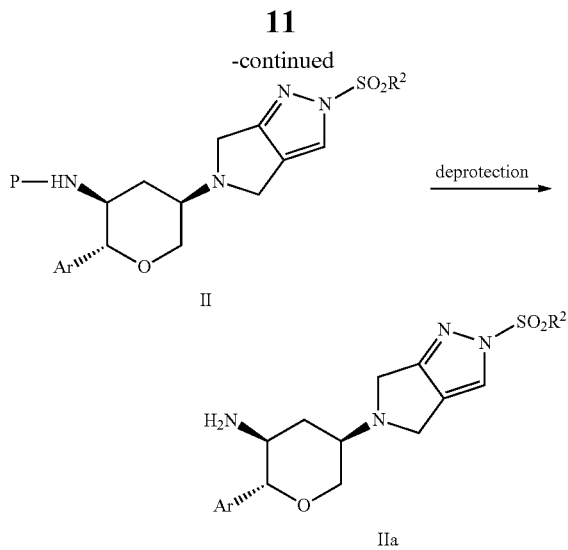

As used in the structural formulas of the compounds described herein, $R^2$ is selected from the group consisting of $C_{1-6}$ alkyl and $C_{3-6}$ cycloalkyl. In one embodiment, $R^2$ is $C_{1-6}$ alkyl. Suitable alkyls include, but are not limited to, methyl, ethyl, propyl, i-propyl, butyl, pentyl and hexyl. In another embodiment, $R^2$ is $C_{3-6}$ cycloalkyl. Suitable cycloalkyls include, but are not limited to, cyclopropyl, cyclobutyl, cyclopentyl and cyclohexyl.

The first step is to de-protect and form a salt of the compound of formula I. The second step is to use the salt form of the compound of formula I and a suitable ketone to from the compound of formula II through a reductive amination process. The final step it to remove the protecting group of the compound of formula II to form a compound of formula IIa.

In certain embodiments, the compounds described herein, have an amine protecting group. Examples of suitable primary amine protecting groups include, but are not limited to, t-butyloxycarbonyl (Boc), benzyloxycarbonyl (CBz), 9-fluorenylmethyl-oxycarbonyl (FMOC), acetyl, formyl, phthaloyl, benzoyl, phenyl, lower alkyl, such as methyl, ethyl or t-butyl and pivaloyl. Depending on what protecting group is used, methods known in the art can be used to remove the protecting group. Once the protecting group is removed a salt can be formed using methods known in the art. In one embodiment the first step is removal of the protecting group and formation of the salt. One embodiment of the amine protecting group is Boc which is removable under acidic conditions, such as aqueous HCl, BSA, TSA, aqueous sulfuric acid, and trifluoroacetic acid in an organic solvent. Starting from the acid allows for greater operational simplicity.

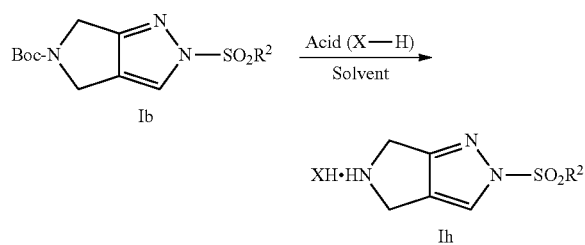

Suitable acids include but are not limited to, sulfuric acid, trifluoroacetic acid, HBr, HCl, $R^5SO_3H$ wherein $R^5$ is hydrogen, $C_{1-6}$ alkyl, $C_{1-6}$ cycloalkyl or aryl. Suitable sulfonic acids include, but are not limited to, methanesulfonic acid, p-toluenesulfonic acid (TSA) and benzenesulfonic acid (BSA). A preferred salt is BSA.

Suitable solvents include, but are not limited to, EtOAc, IPAc, NMP, DMF, DMAc, i-PrAc, MeCN, MeOH, MTBE, PhMe, THF, MeTHF and combinations thereof. A preferred solvent is i-PrAc (of formula 1h, where $X=PhSO_3$).

In one embodiment, the preferred salt is BSA and the solvent is i-PrAc resulted in the pyrazole BSA salt.

The pyrazole salt is then combined with a suitable ketone to form the compound of formula II through a reductive amination process. Suitable reducing agents to mediate the reductive amination include, but are not limited to, sodium triacetoxyborohydride, sodium cyanoborohydride, sodium borohydride, and decaborane. The resulting compound is then de-protected to form a compound of formula IIa. The compound of formula IIa can be further purified. A preferred purification method is re-crystallization of formula IIa. The purification step removes both organic impurities and inorganic impurities, and sets the final form and particle attributes prior to formulation. Re-crystallization can be done in any suitable solvent system, suitable solvents include, but are not limited to, EtOAc, i-PrAc, NMP, DMF, DMAc, MeCN, MeOH, MTBE, PhMe, THF, heptane, hexanes, MeTHF or combinations thereof. In one embodiment purification of a compound of formula II from (Form II) to (Form I) with particle size control is done in a THF/heptane solvent system.

Representative experimental procedures utilizing the novel process are described below. For purposes of illustration, the following Examples are directed to the preparation of 2-(Methylsulfonyl)-2,4,5,6-tetrahydropyrrolo[3,4-c]pyrazole. However, the invention is not limited to the specific reactants and reaction conditions in the example described below.

Abbreviations:
Ar=aryl
Boc=tert-butyloxycarbonyl
Bs=benzenesulfonyl
CDI=1,1'-carbonyldiimidazole
$CH_2Cl_2$=dichloromethane
Cp=cyclopentadienyl
$Cs_2CO_3$=cesium carbonate
d=day(s)
DABCO=1,4-diazabicyclo[2.2.2]octane
DBU=1,8-diazabicyclo[5.4.0]undec-7-ene
DMAC=N,N-Dimethylacetamide
DMAP=4-Dimethylaminopyridine
DMF=N,N-dimethylformamide
DMS=dimethylsulfide
Et=ethyl
EtOAc=ethyl acetate
h=hour(s)
HPLC=high-performance liquid chromatography
i-PrAc=isopropyl acetate
iPr=isopropyl
iPrMgCl=isopropylmagnesium chloride
L=liter(s)
$K_3PO_4$=potassium phosphate
$K_2CO_3$=potassium carbonate
KOtBu=potassium t-butoxide
LDA=lithium diisopopylamide
MeCN=acetonitrile
Me=methyl
MeOH=methanol
MeTHF=methyl
min=minute(s)
mL=milliliter(s)
Ms=mesyl MTBE=methyl tert-butyl ether
Na$_2$CO$_3$=sodium carbonate
NMP=N-Methyl-2-pyrrolidone
Ph=phenyl
PhMe=phenylmethyl
rt=room temperature
t-amylOH=t-Amyl alcohol
TEA=triethylamine
THF=tetrahydrofuran
TMG=1,1,3,3-tetramethylguanidine Certain starting materials and reagents are either commercially available or known in the chemical scientific or patent literature. Purification procedures include, for example, distillation, crystallization, and normal or reverse phase high performance liquid chromatography.

SCHEME I

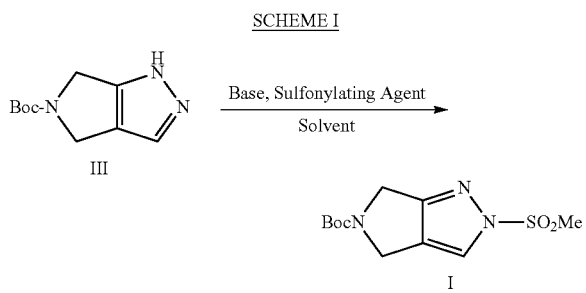

A compound of formula III is added to the base and solvent. The sulfonylating agent is added, with cooling. The bath is removed after addition is complete. The reaction is stopped after conversion is complete.

SCHEME II

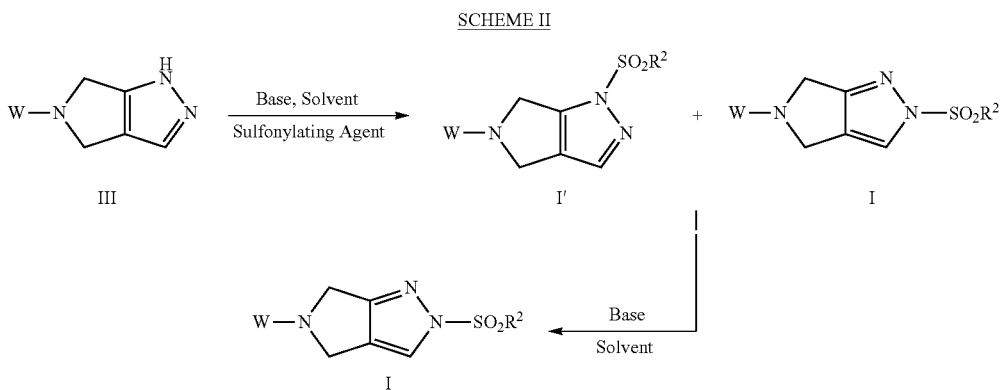

A compound of formula III is added to the base and solvent. The sulfonylating agent is added, with cooling. The bath is removed after addition is complete. The reaction is stopped after conversion is complete. The resulting mixture of I' and I is obtained and a second base and solvent was added.

Example 1

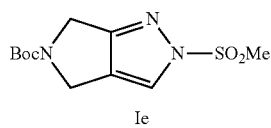

A 100 mL flask was charged with 2.09 g of the pyrazole of formula IIIa and 21 ml DMF. The resulting solution was cooled and 16.5 mL of NaHMDS solution (1.0M in THF) was added such that T$_i$<−12° C. The solution was then cooled to T$_i$=−20° C. 1.718 g of MsCl was then added over 4 h. The resulting solution was aged 16 h at T$_i$=−20° C., leading to 95% conversion and 22:1 selectivity.

The reaction was quenched with water (40 mL). The resulting solution was transferred to a separatory funnel and extracted with i-PrAc (30 mL). After separating the phases, the aqueous/DMF phase was extracted with i-PrAc (10 mL). The combined i-PrAc phases were assayed for 2.5 g total product (83% AY).

The i-PrAc solution was washed with 10% LiCl (2×5 mL), then brine (5 mL). The organic phase was dried over MgSO$_4$, filtered and concentrated to 7 mL total volume. This was transferred to a 50 mL flask with, along with 1 mL of i-PrAc. Seeding induced crystallization. n-Heptane (14 mL) was added over 2 h. The resulting slurry was aged 14 h. The product was isolated by filtration. LC-MS: 288.25 (M+1).

Example 2

Step 1

-continued

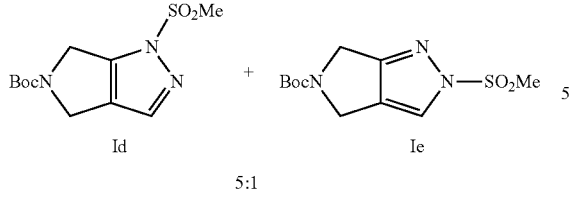

5:1

-continued

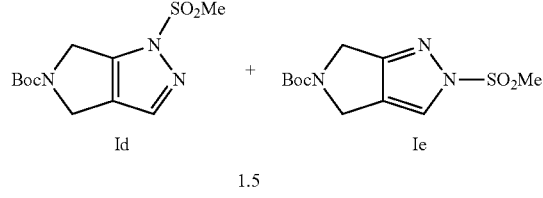

1.5

A 50 mL flask was charged with Ma (2.09 g), MeTHF (16 mL) and Et₃N (1.21 g) and the resulting solution was cooled in an ice bath. MsCl (1.26 g) was added slowly. When addition was complete, the solution was aged for 10 min., resulting in >99% conversion.

The reaction was quenched with water (6 mL), and aqueous phase was discarded. The organic phase was washed with saturated brine (4 mL). The organic phase was dried over MgSO₄, then filtered and subjected to solvent switch into DMAc. LC-MS: 288.25 (M+1).

Step 1 was carried out in MeTHF with MsCl and Et₃N as described in Example 2. Following the workup, the solution was dried via distillation with MeTHF under constant volume/azeotrope conditions to a final volume of (15 mL), and carried forward to step 2. LC-MS: 288.25 (M+1).

Step 2

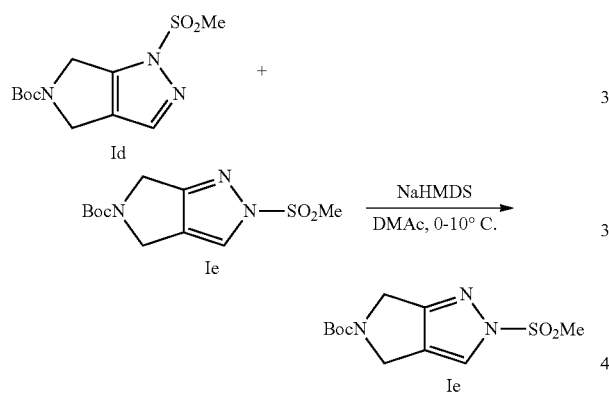

Step 2

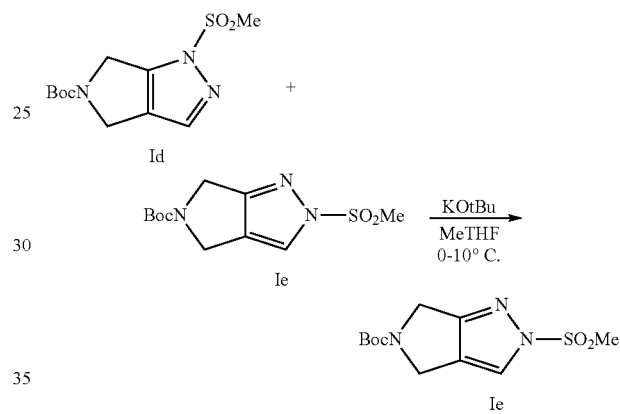

A 50 ml jacketed vessel was charged with the DMAc (12 mL) solution, which was cooled to $T_i$=−10° C. The NaHMDS solution (0.5 mL in THF) was added. The resulting solution was aged 16 h at $T_i$=−10° C. The ratio of Ie:Id was then 96:4. The reaction was quenched with 1 mL of 15% citric acid, followed by the slow addition of H₂O (16 mL). After 2 h, the crystalline product Ie was isolated by filtration. The cake was displacement washed with 6:4 H₂O:DMAc (10 mL), then H₂O (10 mL). Drying afforded 2.15 g of Ie. LC-MS: 288.25 (M+1).

A 50 ml jacketed vessel was charged with the dried MeTHF (12 mL) solution, which was cooled to $T_i$=−10° C. KOtBu (0.056 g) was added as a solid.

After 3 h the solution was quenched with 15 wt % aq. citric acid (2.5 mL), and then warmed to room temperature. The phases were separated, and the aqueous phase was extracted with MeTHF (2 mL). The combined organic phases were washed with half-brine (4 mL), then dried over MgSO₄ and filtered. The resulting solution was assayed: 2.43 g desired product 1e (85% yield). LC-MS: 288.25 (M+1).

Example 3

Step 1

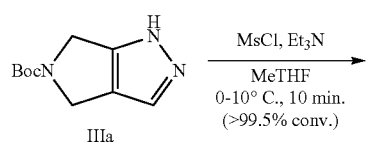

Example 4

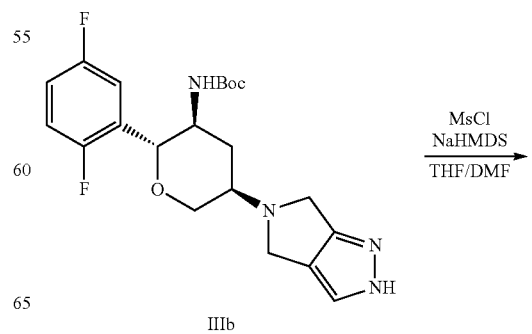

-continued

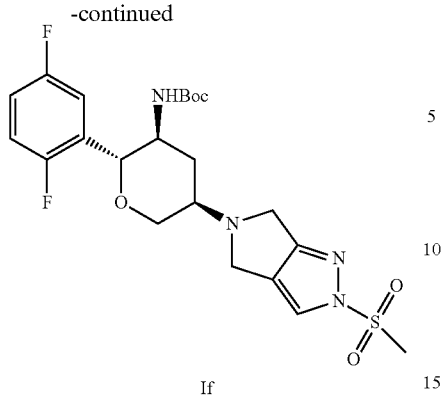

If

-continued

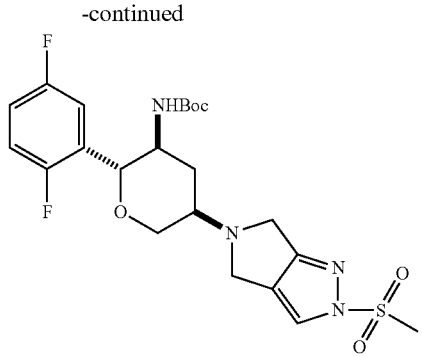

If

A 1 L reaction vessel was charged with pyrazole IIIb (33.9 g, 81.0 mmol) and DMF (362 mL). The resulting solution was cooled to $T_j=-15°$ C. and the NaHMDS solution (133 mL of 1.0 M in THF) was added over 30 minutes. After completion of the NaHMDS charge, the solution was stirred at $T_j=-15°$ C. for 20 minutes. Methanesulfonyl chloride (10.04 mL, 129 mmol) was added over 5 hours. The reaction was aged for an additional 12 h. The reaction temperature was adjusted to $T_j=0°$ C., and water (108 mL) was then added over 1 h. The solids were filtered. The cake was subjected to displacement wash with 1:1 DMF:water (125 mL), followed by displacement wash with water (108 mL).

After vacuum drying, the product was collected from the filter pot. The yield was 31.9 g of If (79% yield). LC-MS: 499.10 (M+1).

Example 5

Step 1

A 1 L reaction vessel was charged with pyrazole IIIb (10.0 g, 22.6 mmol) and DCM (180 mL). The resulting solution was mechanically stirred at ambient temperature. Triethylamine (3.43 g, 33.9 mmol) was then added. The solution was stirred at ambient temperature for 20 minutes, and subsequently was cooled to $T_j=0°$ C. Methanesulfonyl chloride (3.36 g, 29.4 mmol) was added over 15 minutes. Upon completion of the charge, the reaction was aged at ambient temperature and stirred for 20 minutes.

The reaction was quenched with 1N HCl (180 mL), and was transferred to a separatory funnel. After separating the phases, the organic DCM layer was washed with water (180 mL). The DCM was removed by rotary evaporation and the product mixture was solvent switched into THF (300 mL total volume). The heterogeneous mixture of Ig and If (If:Ig=1:9) in THF was carried to Step 2. LC-MS: 499.10 (M+1).

Step 2

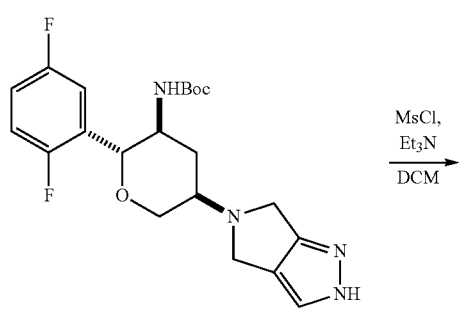

IIIb

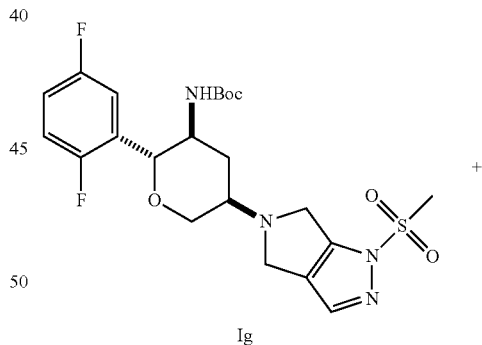

Ig

+

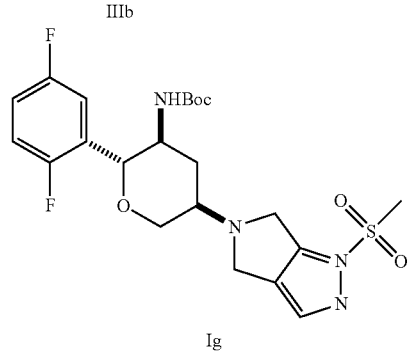

Ig

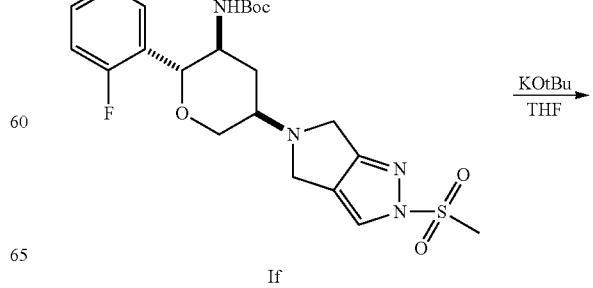

If

-continued

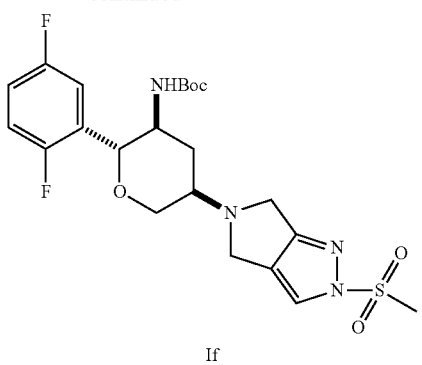

If

A 500 mL vessel was charged with the Ig/If slurry. A solution of KOtBu in THF (9.5 mL of 1M solution, 9.5 mmol) was then added. The resulting solution was stirred for 16 h, resulting in a ratio of If:Ig=99:1. Heptane (80 mL) was then added to the reaction slurry over 30 minutes.

The solids were filtered. The cake was subjected to displacement wash with 9:1 THF:heptane (10 mL), followed by displacement wash with heptane (10 mL). After vacuum drying, the product was collected from the filter pot. The yield was 8.4 g of If (75% yield). The final product displayed a ratio of If:Ig=1637:1. LC-MS: 499.10 (M+1).

Example 6

Formation of Salt

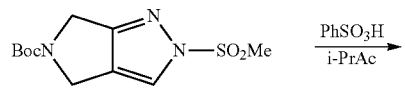

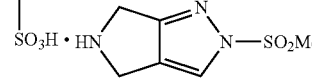

A 300 mL flask was charged with 16.18 g of the Boc-protected mesylated pyrazole and i-PrAc (110 mL). Benzenesulfonic acid was added as a solution in i-PrAc (40 mL). After addition was complete, the solution was heated to $T_i$=30° C. for 2 h. The reaction was then cooled gradually to ambient temperature and stirred for 14 h. The slurry was filtered. The cake was washed with i-PrAc (40 mL). The cake was then dried for 6 h. 19.5 g of a white solid was collected. $^1$H NMR (400 Mhz, $d_6$-dmso): δ 9.80 (s, 2H), 8.13 (s, 1H), 7.63-7.57 (m, 2H), 7.35-7.28 (m, 2H), 4.43 (s, 2H), 4.36 (s, 2H), 3.58 (s, 3H); LC-MS: 188.20 (M+1).

Example 7

Step I

Reductive Amination

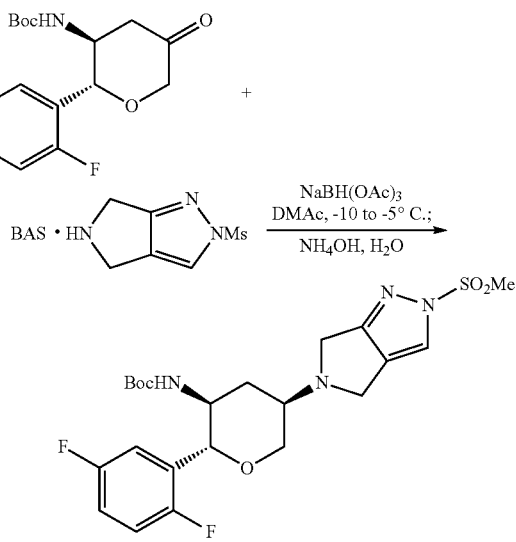

A 500 mL 3-neck flask (equipped with overhead stirring, a $N_2$ inlet, and a thermocouple) was charged with the 8.25 g of the ketone, 9.8 g of the pyrazole salt of Example 4, and 124 mL of DMAc, and the resulting homogeneous solution was cooled to $T_i$=−10° C. 6.94 g of NaBH(OAc)$_3$ was added portion-wise as a solid. The reaction was aged at $T_i$=−10° C. until the ketone consumption met the specification of ≥98%. The reaction slurry was quenched with a mixture of NH$_4$OH (8.3 mL) and H$_2$O (16.5 mL), via slow addition. The resulting slurry was heated to $T_i$=50° C. and then cooled to $T_i$=22° C.

The slurry was filtered. The cake was subjected to a displacement wash with 5:1 DMAc:H$_2$O (65 mL), followed by a displacement wash with H$_2$O (65 mL). The cake was dried until the amount of residual H$_2$O was ≤10%. 10.6 g of off white solids were recovered (93.5% purity). LC-MS: 499.10 (M+1).

Step II

Boc-Deprotection

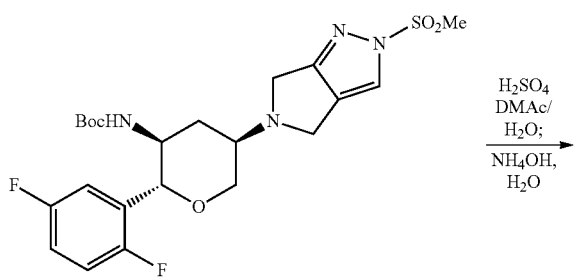

-continued

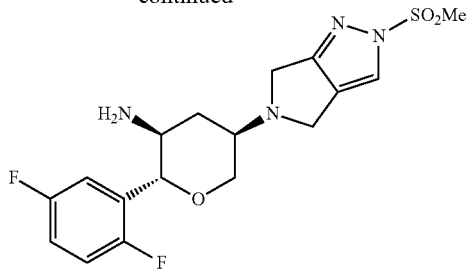

A 200 mL 3-neck jacketed flask (equipped with overhead stirring, a $N_2$ inlet, and a thermocouple) was charged with the reductive amination product (10.35 g) and DMAc (31 mL) and water (41.4 mL), and the resulting slurry was stirred at $T_i=20°$ C. A solution of $H_2SO_4$ (12.2 mL; 12 equivalents) and $H_2O$ (20.7 mL) was added slowly over 3.5 hours. The resulting slurry was aged for 15 hours. The solution was then cooled to $T_i=0-5°$ C. $NH_4OH$ was added until the pH of the supernatant was 10.2. The slurry was cooled and filtered. The wetcake was subjected to displacement wash with cold $H_2O$ (17.5 mL), followed by a slurry wash with $H_2O$ (17.5 mL).

The recovered solids were dried, affording 6.73 g (98.8% purity, 88.6% yield) of a solid. $^1$H NMR (500 MHz, $CD_3OD$): 1.71 (q, 1H, J=12 Hz), 2.56-2.61 (m, 1H), 3.11-3.18 (m, 1H), 3.36-3.40 (m, 1H), 3.48 (t, 1H, J=12 Hz), 3.88-3.94 (m, 4H), 4.30-4.35 (m, 1H), 4.53 (d, 1H, J=12 Hz), 7.14-7.23 (m, 2H), 7.26-7.30 (m, 1H), 7.88 (s, 1H). LC-MS: 399.04 (M+1).

Example 8

Recrystallization: A reaction vessel was charged with THF (300 mL) and 38.8 g of the compound of Example 7. The solution was heated to $T_i=55°$ C. and was filtered. The resulting solution was seeded and aged for 1 hr at $T_i=45°$ C. and then gradually cooled to ambient temperature. The slurry was concentrated to ~200 mL and n-heptane (380 mL) was added slowly. The solids were collected by filtration, and were subjected to displacement wash with 2:1 n-heptane:THF (120 mL), followed by a displacement wash with n-heptane (80 mL). Drying afforded 34.8 g of the product (form I).

Example 9

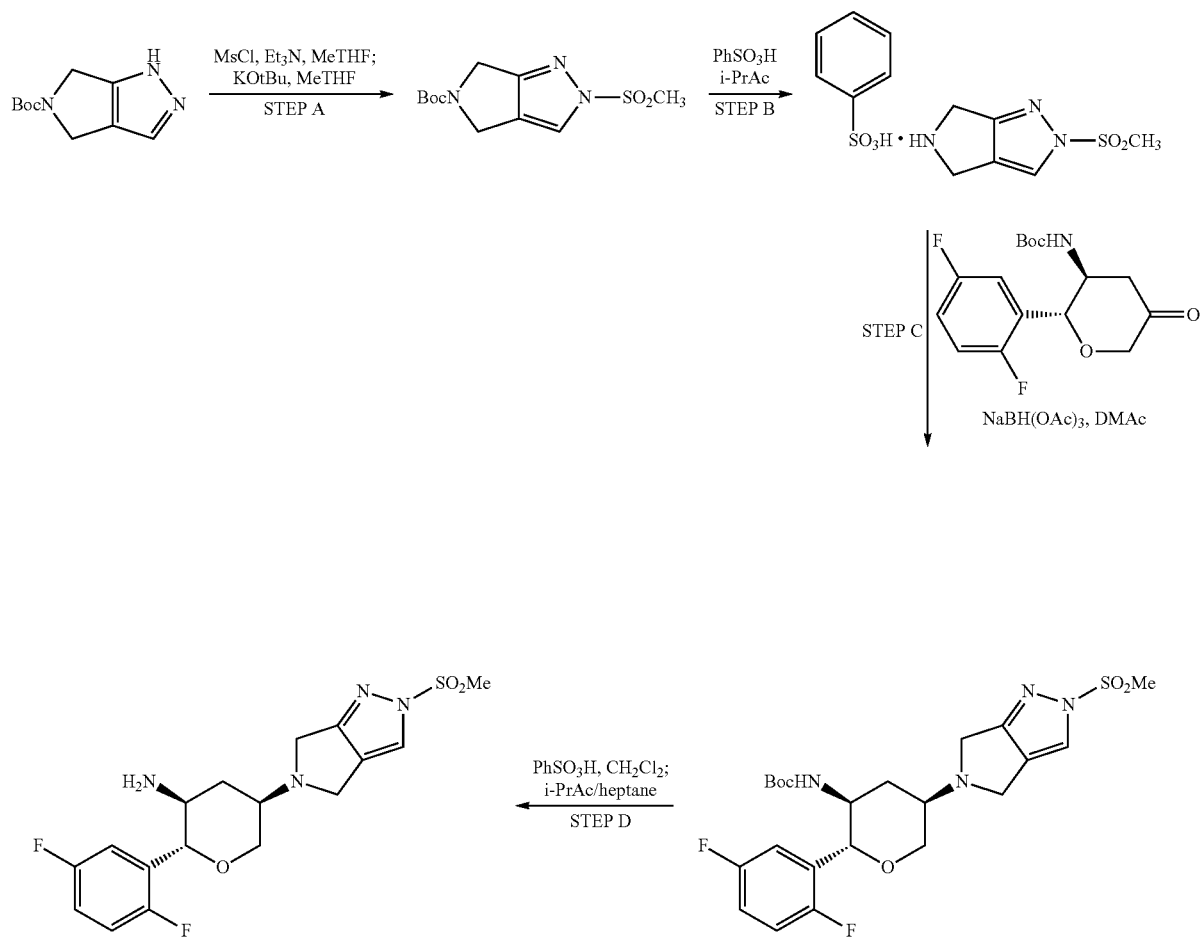

Step A:

A solution of tert-butyl 4,6-dihydropyrrolo[3,4-c]pyrazole-5(1H)-carboxylate (30.0 kg, 143 mol) in 2-methyltetrahydrofuran (384 kg) was prepared. Triethylamine (25.0 g, 0.247 mol) was added and the batch cooled to −10-5° C. Then, methanesulfonyl chloride (21.4 kg, 187 mol) was slowly added over 2 h. After stirring for 1 h at room temperature, water (150 kg) was added drop-wise at 5-15° C. This was followed by addition of 1N HCl solution until the pH was 7. The resulting layers were separated and the aqueous extracted with 2-methyltetrahydrofuran (106 kg). The combined organics were washed with saturated brine (2×150 kg), dried with Na$_2$SO$_4$, filtered, and concentrated to 60-90 L.

The resulting crude was dissolved in 2-methyltetrahydrofuran (381 kg) and charged with a solution of potassium tert-butoxide in THF (805 g in 6.6 kg THF). After stirring 1 h at room temperature under nitrogen, more potassium tert-butoxide in THF (329 g in 3.0 kg THF) was added and stirred for 1 h. Analytical analysis indicates that tert-butyl 2-(methylsulfonyl)-2,6-dihydropyrrolo[3,4-c]pyrazole-5(4H)-carboxylate is the major regioisomer, so saturated brine (154 kg) was then added. After brief agitation, the layers were separated and the organics were washed with saturated brine (2×155 kg). The combined aqueous waste layers were then extracted with 2-methyltetrahydrofuran (103 kg). The combined organics were treated with activated carbon (8.75 kg), filtered, and dried with Na$_2$SO$_4$. This was then filtered and concentrated to 60-90 L. This slurry was then heated to dissolve solids at 40-50° C. and n-heptane was added (34 kg). After cooling to room temperature for 2-4 h, n-heptane (156 kg) was added and the slurry was then aged for 2-4 h at 0-5° C. The slurry was filtered and the cake washed with n-heptane. The solids were dried under vacuum at 45-55° C. to give tert-butyl 2-(methylsulfonyl)-2,6-dihydropyrrolo[3,4-c]pyrazole-5(4H)-carboxylate.

Step B:

To a solution of tert-butyl 2-(methylsulfonyl)-2,6-dihydropyrrolo[3,4-c]pyrazole-5(4H)-carboxylate (32.1 kg, 111 mol) in iso-propylacetate (289 kg) was added benzenesulfonic acid (35.35 kg, 223 mol). The reaction was stirred for 3 days at room temperature and then cooled to 0-10° C. and stirred an additional 1 h. The resulting slurry was filtered and the cake washed with iso-propylacetate. The solids were dried overnight under vacuum at room temperature to give 2-(methylsulfonyl)-2,4,5,6-tetrahydropyrrolo[3,4-c]pyrazol-5-ium benzenesulfonate.

Step C:

A vessel was charged with N,N-dimethylacetamide (520.6 kg), 2-(methylsulfonyl)-2,4,5,6-tetrahydropyrrolo[3,4-c]pyrazol-5-ium benzenesulfonate (30.0 kg, 86.8 mol), and tert-butyl[(2R,3S)-2-(2,5-difluorophenyl)-5-oxotetrahydro-2H-pyran-3-yl]carbamate (131.2 kg, 95.3 mol). After dissolving at room temperature, the solution was cooled to 0-10° C. and sodium triacetoxyborohydride (24 kg, 113 mol) was added in four equal portions every 40 min. The reaction was then allowed to warm to room temperature and stirred an additional 5 h. The solution was then cooled to 5-15° C. and water (672 kg) was added over 1-2 h. The resulting slurry was filtered and the cake washed sequentially with N,N-dimethylacetamide, twice with water, and then n-heptane. The solids were dried to give tert-butyl {(2R,3S,5R)-2-(2,5-difluorophenyl)-5-[2-(methylsulfonyl)-2,6-dihydropyrrolo[3,4-c]pyrazol-5(4H)-yl]tetrahydro-2H-pyran-3-yl}carbamate.

Step D:

Benzenesulfonic acid (32.95 kg, 271 mol) was dissolved in dichloromethane (1020 kg) under nitrogen. Then, 880 g of water was added such that the solution KF was 0.2%. Next, tert-butyl {(2R,3S,5R)-2-(2,5-difluorophenyl)-5-[2-(methylsulfonyl)-2,6-dihydropyrrolo[3,4-c]pyrazol-5(4H)-yl]tetrahydro-2H-pyran-3-yl}carbamate (38.4 kg, 100 mol) was added in three equal portions over 30 min. The reaction was then aged overnight at room temperature. Next, water (733 kg) was added over 1 h and the reaction stirred rapidly for 1 h. The layers were then separated, discarding the resulting organics layer. To the aqueous layer was charged dichloromethane (510 kg) followed by triethylamine (22.4 kg, 592 mol). After agitation, the layers were separated and the aqueous extracted with dichloromethane (510 g). The combined organics were washed with 7% aqueous NaHCO$_3$ (2×410 kg) and 5% brine (386 kg). The organics were then dried with Na$_2$SO$_4$, filtered, and treated with activated carbon (6.2 kg of C-941). The carbon was filtered off and the filtrate was concentrated under vacuum to 154-193 L. This solution was then warmed to 30-35° C. Next, iso-propylacetate (338 kg) was added and the solution stirred at room temperature for 1.5 h. Then, n-heptane (159 kg) was charged to the vessel drop-wise and stirred for 3 h. The slurry was then filtered and the cake washed with n-heptane. This wet cake was then recrystallized again by dissolving it into dichloromethane and adding iso-propylacetate and n-heptane as before, filtering, and washing with n-heptane. The solids were dried under vacuum at to give crystalline (2R,3S,5R)-2-(2,5-Difluorophenyl)-5-[2-(methylsulfonyl)-2,6-dihydropyrrolo[3,4-c]pyrazol-5(4H)-yl]tetrahydro-2H-pyran-3-amine was washed with cold 2:1EtOAc/hexanes to give the title compound as a solid. $^1$H NMR (500 MHz, CD$_3$OD): 1.71 (q, 1H, J=12 Hz), 2.56-2.61 (m, 1H), 3.11-3.18 (m, 1H), 3.36-3.40 (m, 1H), 3.48 (t, 1H, J=12 Hz), 3.88-3.94 (m, 4H), 4.30-4.35 (m, 1H), 4.53 (d, 1H, J=12 Hz), 7.14-7.23 (m, 2H), 7.26-7.30 (m, 1H), 7.88 (s, 1H). LC-MS: 399.04 [M+1].

What is claimed is:

1. A process for preparing a compound of structural formula I:

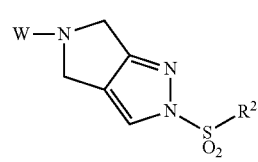

wherein R$^2$ is selected from the group consisting of:
    C$_{1-6}$ alkyl and C$_{3-6}$ cycloalkyl; and
W is hydrogen; P, wherein P is an amine protecting group; or

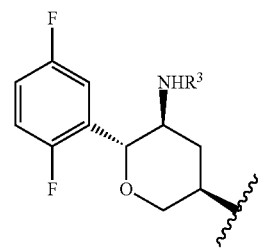

wherein R$^3$ is hydrogen or P, wherein P is an amine protecting group;

comprising sulfonylation of a compound of formula III:

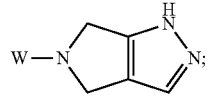

and
isomerization of a mixture of compounds of formula I' and formula I:

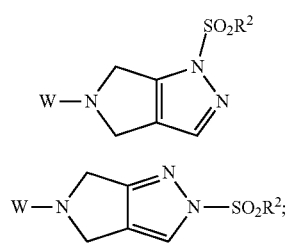

wherein the sulfonylation of a compound of formula III and isomerization of the sulfonylated formula III comprises mixing a compound of formula III with a sulfonylating agent and at least one base in at least one suitable organic solvent.

2. The process of claim 1, wherein in the process is done as a single-step process.

3. The process of claim 2, wherein the sulfonylation of the compound of formula III and isomerization of the intermediate mixture of sulfonylated compounds of formula I and I' comprises combining the compound of formula III, a sulfonylating agent and a suitable base in a suitable solvent.

4. The process of claim 3 wherein the sulfonylating agent is MsCl, the base is NaHMDS and the solvent comprises a mixture of THF and DMF.

5. The process of claim 1, wherein the process is done as a two-step process.

6. The process of claim 5, wherein the first step is sulfonylation of the compound of formula III comprising mixing the compound of formula III, a sulfonylating agent, and a first base in a suitable first solvent.

7. The process of claim 6, wherein the sulfonylating agent is MsCl, the first base is TEA and the first solvent is MeTHF.

8. The process of claim 7, wherein the second step is isomerization of the mixture of compounds of formula I and formula I' comprising mixing the mesylated compound of formula III, and a second base in a suitable second solvent.

9. The process of claim 8, wherein the second base is KOtBu or NaHMDS and the second solvent is MeTHF or DMAc.

10. The process of claim 1 wherein greater than 70% conversion to formula I is achieved.

* * * * *